(12) United States Patent
Laurila et al.

(10) Patent No.: US 7,200,200 B2
(45) Date of Patent: Apr. 3, 2007

(54) X-RAY FLUORESCENCE MEASURING SYSTEM AND METHODS FOR TRACE ELEMENTS

(75) Inventors: Melvin J. Laurila, Georgetown, KY (US); Claus C. Bachmann, Bad Wilbad (DE)

(73) Assignee: Quality Control, Inc., Georgetown, KY (US)

( * ) Notice: Subject to any disclaimer, the term of this patent is extended or adjusted under 35 U.S.C. 154(b) by 263 days.

(21) Appl. No.: 10/488,723

(22) PCT Filed: Sep. 3, 2002

(86) PCT No.: PCT/US02/27815

§ 371 (c)(1),
(2), (4) Date: Mar. 3, 2004

(87) PCT Pub. No.: WO03/021244

PCT Pub. Date: Mar. 13, 2003

(65) Prior Publication Data

US 2004/0240606 A1 Dec. 2, 2004

Related U.S. Application Data

(60) Provisional application No. 60/317,257, filed on Sep. 4, 2001.

(51) Int. Cl.
*G21N 23/223* (2006.01)

(52) U.S. Cl. .................. 378/45; 378/47; 250/269.3
(58) Field of Classification Search .............. 378/45, 378/47; 250/269.3
See application file for complete search history.

(56) References Cited

U.S. PATENT DOCUMENTS 2,225,940 A * 12/1940 Grossmann ............... 378/98

(Continued)

FOREIGN PATENT DOCUMENTS

GB  1070337  6/1967

OTHER PUBLICATIONS

Nguyen, T.H. et al. "Mercury analysis in environmental samples by EDXRF and CV-AAS"; Fresenius J Anal Chem (1998) 360: 199-204.*

(Continued)

*Primary Examiner*—Edward J. Glick
*Assistant Examiner*—Thomas R. Artman
(74) *Attorney, Agent, or Firm*—King & Schickli, PLLC

(57) ABSTRACT

An X-ray fluorescence measuring system and related measuring methods are disclosed, the system using X-ray energy at a level of less than 80 KeV may be directed toward a material, such as coal. The energy fluoresced may be detected (10) and used to measure the elemental composition of the material, including trace elements. The material may be moving or stationary.

45 Claims, 11 Drawing Sheets

U.S. PATENT DOCUMENTS

| | | | |
|---|---|---|---|
| 2,642,537 A * | 6/1953 | Carroll et al. | 378/50 |
| 3,404,275 A * | 10/1968 | Martinelli | 378/46 |
| 3,411,001 A * | 11/1968 | Wilchinsky | 378/75 |
| 3,496,353 A * | 2/1970 | Rhodes | 378/45 |
| 3,678,268 A * | 7/1972 | Reim et al. | 378/54 |
| 3,843,881 A * | 10/1974 | Barton et al. | 250/269.1 |
| 3,864,570 A | 2/1975 | Zingaro | |
| 3,980,882 A | 9/1976 | Carr-Brion et al. | |
| 4,015,124 A | 3/1977 | Page | |
| 4,029,963 A * | 6/1977 | Alvarez et al. | 378/5 |
| 4,090,074 A | 5/1978 | Watt et al. | |
| 4,283,625 A * | 8/1981 | King | 378/45 |
| 4,486,894 A | 12/1984 | Page et al. | |
| 4,550,768 A | 11/1985 | McMullen et al. | |
| 4,566,114 A | 1/1986 | Watt et al. | |
| 4,582,992 A | 4/1986 | Atwell et al. | |
| 4,698,835 A * | 10/1987 | Ono et al. | 378/136 |
| 4,882,927 A | 11/1989 | Gould | |
| 5,020,084 A * | 5/1991 | Robertson | 378/46 |
| 5,048,761 A | 9/1991 | Kim | |
| 5,065,416 A | 11/1991 | Laurila et al. | |
| 5,261,977 A | 11/1993 | Powell | |
| 5,274,688 A * | 12/1993 | Grodzins | 378/45 |
| 5,359,639 A * | 10/1994 | Saito | 378/4 |
| 5,406,608 A * | 4/1995 | Yellepeddi et al. | 378/46 |
| 5,497,407 A * | 3/1996 | Komatsu et al. | 378/45 |
| 5,646,354 A | 7/1997 | Lovejoy | |
| 5,729,013 A * | 3/1998 | Bergren, III | 250/255 |
| 5,745,543 A * | 4/1998 | De Bokx et al. | 378/45 |
| 5,750,883 A | 5/1998 | Elder | |
| 5,867,553 A * | 2/1999 | Gordon et al. | 378/4 |
| 6,122,344 A * | 9/2000 | Beevor | 378/88 |
| 6,130,931 A | 10/2000 | Laurila et al. | |
| 6,266,390 B1 | 7/2001 | Sommer, Jr. et al. | |
| 6,519,315 B2 * | 2/2003 | Sommer et al. | 378/45 |
| 6,522,718 B2 * | 2/2003 | Sato | 378/50 |
| 6,765,986 B2 * | 7/2004 | Grodzins et al. | 378/46 |

OTHER PUBLICATIONS

A.C. Huber, J.A. Pantazis, V. Jordanov, "High Performance, Thermoelectrically Cooled X-Ray and Gamma Ray Detectors" Nuclear Instruments and Methods in Physics Research B 99 (1995), pp. 665-668.

Ken Carr-Brion, "On-Line X-Ray Fluorescence Analysis of Liquids, Slurries and Pastes" X-Ray Analysers in Process Control, Chapter 3, pp. 38-45, 80-85.

Process Technology, Inc., "SBIR Phase I Final Report 'Development of a Coal Sulfur Analysis and Control System,'" Contract No. DE-FG02-92ER81394, May 24, 1993, 31 pps.

* cited by examiner

X-RAY FLUORESCENCE MEASURING SYSTEM AND METHODS FOR TRACE ELEMENTS

This application claims the benefit of U.S. Provisional Patent Application Ser. No. 60/317,257, filed Sep. 4, 2001, the disclosure of which is incorporated herein by reference.

FIELD OF THE INVENTION

In one aspect, this invention relates to measuring elements present in coal, ores, and other substances using energy dispersive X-ray fluorescence (XRF) spectroscopy. In another aspect, the invention relates to different apparatuses and methods for use in conjunction with elemental analyzers.

BACKGROUND OF THE INVENTION

Techniques for analyzing or measuring the elemental composition of a substance, such as coal, using X-ray fluorescence (XRF), are well-known in the art. An example of one technique is disclosed in U.S. Pat. No. 6,130,931, the disclosure of which is incorporated herein by reference. While these XRF techniques work extraordinary well for measuring certain elements, such as sulfur, the ability to measure "trace elements" (e.g., vanadium, chromium, manganese, cobalt, nickel, copper, zinc, arsenic, selenium, and molybdenum) has previously been limited to laboratory techniques involving extensive preparation using pulverized samples. For instance, ASTM Standard Test Method D4606 for the determination of arsenic and selenium in coal by the Hydride Generation/Atomic Absorption Method analyzes a 1.0 gram sample of coal pulverized to pass a 250 mm standard sieve. ASTM Standard Test Method D6357 for the Determination of Trace Elements in Coal, Coke, and Combustion Residues from Coal Utilizations Processes by Inductively Coupled Plasma Mass Spectrometry and Graphite Furnace Atomic Absorption Spectrometry analyzes a 0.5 gram sample of coal ash ground to pass 150 μm. The wet chemistry methods dictated by standard laboratory methods are time consuming and can only produce a single analysis in a matter of hours. Turn around time in commercial laboratories is often days or weeks and the analysis is very expensive.

U.S. Pat. No. 5,020,084 to Robertson, which is also incorporated herein by reference, proposes the use of X-ray energy at a level of 100–130 kilo-electron-volts (KeV) to measure a finely divided heavy metal (gold) dispersed in a non-metallic matrix using K emission bands. However, this patent does not mention the use of low energy XRF to measure trace elements, including gold. Moreover, it dismisses L emission XRF techniques as inaccurate. Furthermore, high energy XRF cannot be used to detect the K emission bands of the lighter trace elements with atomic numbers less than or equal to 48 (Cadmium). Thus, the approach taught in the Robertson patent is not a solution to the problems identified in the foregoing paragraph.

SUMMARY OF THE INVENTION

In one aspect, the present invention is an on-line sensor or sensing device for measuring (monitoring, detecting, sensing, etc.) one or more elements in a material, including the presence of trace elements down to levels of less than 1 part per million (ppm) or μg/g with relatively short analysis times (possibly as short as 2–6 minutes). This is accomplished using low energy (less than 80 KeV and, more preferably, less than 65 KeV) X-rays to bombard the stream of with X-rays in a bandwidth designed to optimally excite the characteristic K or L emission bands of the element(s) of interest.

Using this system, it is possible to detect fluoresced emissions with energies as low as 1.0 KeV. Consequently, trace elements present in coal (defined by ASTM as those elements whose individual concentrations are generally less than 0.01%) such as vanadium, chromium, manganese, cobalt, nickel, copper, zinc, arsenic, selenium, and molybdenum each have Kα or Kβ emission bands that can be readily measured by this XRF technique. Mercury and lead Lα emission bands can also be measured using this technique. Other metals dispersed in mineral ores in small or trace quantities, such as platinum and gold, can also be measured with low energy XRF, again using the Lα emission bands.

In one embodiment, an adjustable voltage X-ray tube is used as the source. This allows for the incident X-ray energies to be adjusted, preferably to within a range of 1.5–3.0 times the energy of the characteristic emission bands from the elements of interest to maximize the efficiency of emission. It is also possible to use filters to narrow the band of incident X-rays, which further reduces the amount of interference, as well as a slotted collimator for collimating the X-ray energy emitted from the source. Providing an optimal X-ray source:detector (sensor) geometry and positioning the sensor as close as possible to the surface of the material also enhances the results.

In accordance with another aspect of the invention, a sled for supporting a sensor, such as an XRF sensor, adjacent to a moving stream of material is disclosed. The sled is mounted so as to be capable of swinging to and fro in response to changes in the profile of the material. It may also be designed to aid in further compacting the material to help ensure that an accurate reading is taken by the sensor. Other manners of mounting a sensor and, in particular, and XRF sensor are also disclosed, including: (1) mounting the sensor in a probe for positioning in a borehole; and (2) mounting two sensors inline along a moving stream of material, with one sensing trace elements only and the other sensing the "lighter" elements.

BRIEF DESCRIPTION OF THE DRAWING FIGURES

DETAILED DESCRIPTION OF THE INVENTION

Figure 1A:
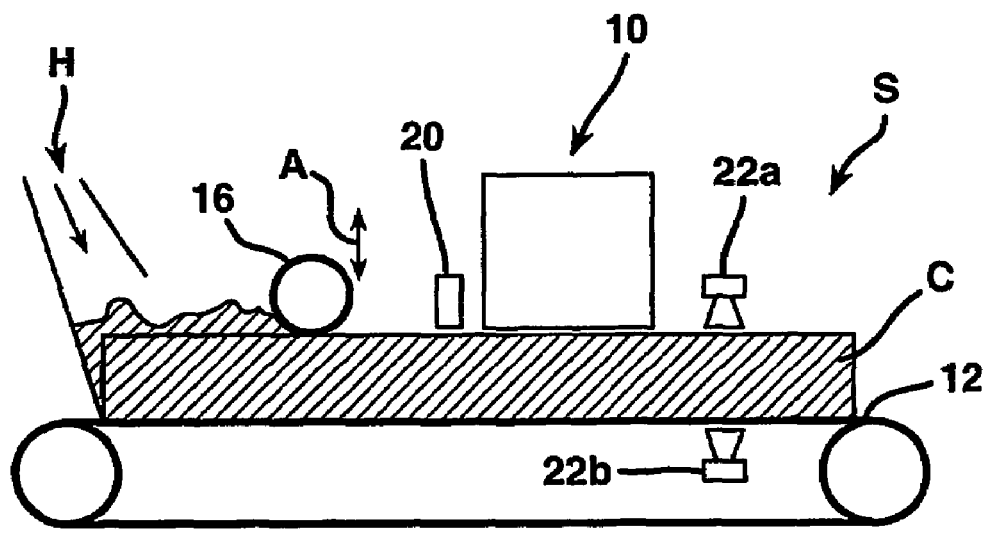
FIGS. 1a and 1b are schematic side views of mechanical sampling systems including the sensor forming one aspect of the present invention.
Figure 1B:
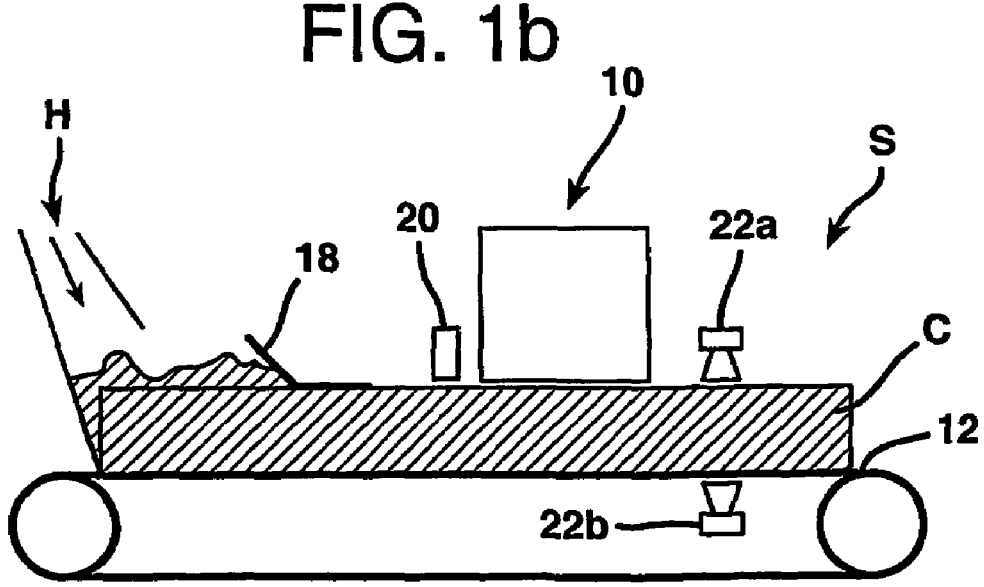

Reference is now made to FIGS. 1a and 1b, which show one embodiment of an XRF trace element sensor 10 mounted adjacent to an endless transfer conveyor belt 12 carrying a substance or material, such as coal C. The belt 12 and sensor 10 in combination may form part of a mechanical sampling system 14 for measuring the elemental composition of a sample of material, such as ore or coal C delivered from a chute H or the like. The sample may be supplied from a main conveyor line (not shown), and is preferably crushed or pulverized to have a particle size of approximately less than or equal to 10 millimeters (⅜ths of an inch) prior to being delivered to the sampling system 14.

In this system 14, a leveling structure and skirting (not shown) along the sides of the belt 10 together help to assure that a constant or substantially constant geometry of coal C or other substance is presented to the sensor 10 forming part of the system 14. In FIG. 1a, the leveling structure is shown as a rotatable drum 16 capable of being moved toward and away from the surface of the belt 12 (note action arrow A), depending on the profile of the material being conveyed. However, the leveling structure of FIG. 1a could also be considered a stationary cylinder that is also movable toward and away from the belt 12. Instead of a rotatable drum or stationary cylinder, a leveling plow 18 could also be used to compact the material, as shown in FIG. 1b. Any combination of these structures could also be used, as could structures not disclosed herein, as long as the function of assuring a level, constant or substantially constant profile is achieved.

A material sensor 20 may also be provided upstream of the elemental sensor 10 for indicating the presence of material on the belt 12. Opposed microwave moisture sensors 22a, 22b may also be positioned adjacent to the belt 12 for providing moisture readings, if desired. As discussed in detail further below, outputs from each of the sensors, as well as from the system 10, may be fed to a remote computer or controller through suitable transmission lines (see FIG. 2) for further use, display, or processing, as necessary or desired to measuring the elemental composition or another characteristic of the material sample.

Figure 2:
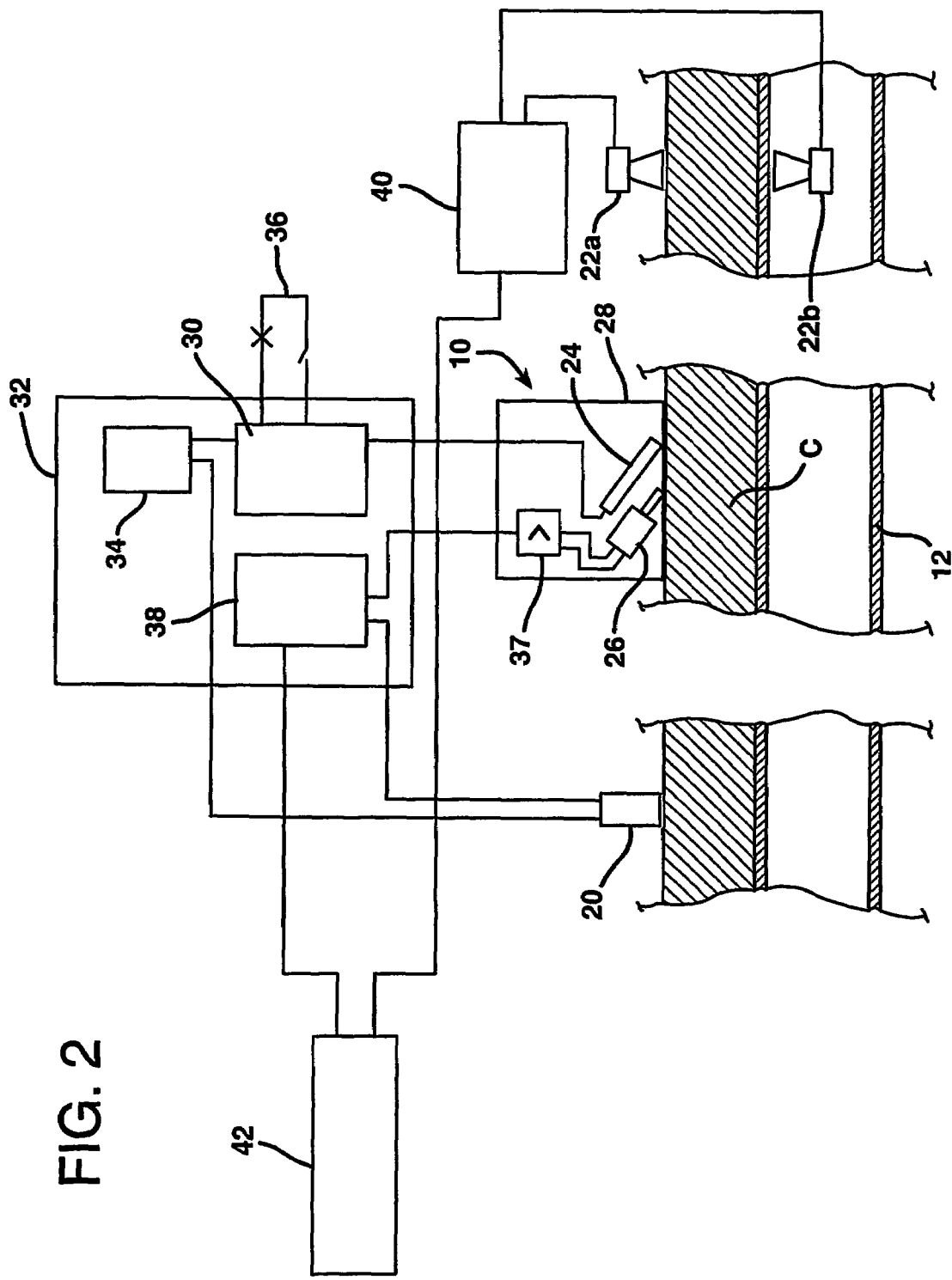
FIG. 2 is a schematic side view similar to FIGS. 1a and 1b showing the system in more detail.

FIG. 2 provides a generally schematic view of the overall arrangement of the sensors 10, 20, 22a, and 22b, with portions of the coal C and the belt 12 cut away for clarity. The elemental sensor 10 includes an X-ray source 24 (typically an X-ray tube) and an X-ray detector 26 (typically an Si-PIN diode) positioned in a backscattering configuration adjacent to the surface of the coal C. The source and detector 24, 26 may be positioned in an instrument enclosure or box 28 having an opening covered by a window (not shown) through which the X-ray energy passes (not shown). The window may be thin (such as 0.9 mil polypropylene) to seal the enclosure 28 from fugitive dust. Since the window will absorb a fraction of the low energy X-rays, the opening may be left open to maximize the transmission of X-rays to the detector 26. When no window is employed, a positive gas pressure (air or other gas, such as helium) may be applied to the instrument enclosure, sufficient to prevent dust from entering.

In a most preferred embodiment, an adjustable voltage X-ray tube is used as the source 24. This allows for the incident X-ray energies to be adjusted, preferably to within the range of 1.5–3.0 times the energy of the characteristic emission bands from the elements of interest to maximize the efficiency of emission.

The X-ray source 24 is connected to a high voltage power supply 30, which may be included as part of a remote "power box" 32 also including power supply 34. As is known in the art, an interlock 36 including a warning light X and a switch may also be associated with the high voltage power supply 30 for safety and security reasons. The power box 32 may also enclose or include the device for receiving an output signal from the X-ray detector 26, such as a multi-channel analyzer (MCA) 38. A pre-amplifier and power source, identified collectively by reference numeral 37 may also be connected to the MCA 38, preferably in the instrument enclosure 28. The MCA 38 may also be coupled to and receive a signal from the material sensor 20. The outputs from the moisture sensors 22a, 22b may be connected to a separate moisture processor 40 capable of receiving and processing the analog signals. Both the MCA 38 and the moisture processor 40 may be coupled to a remote computer 42 for providing an indication of the measurements taken by the sensors (e.g., elemental composition, moisture content, etc.), such as using a monitor or display.

Figure 3A:
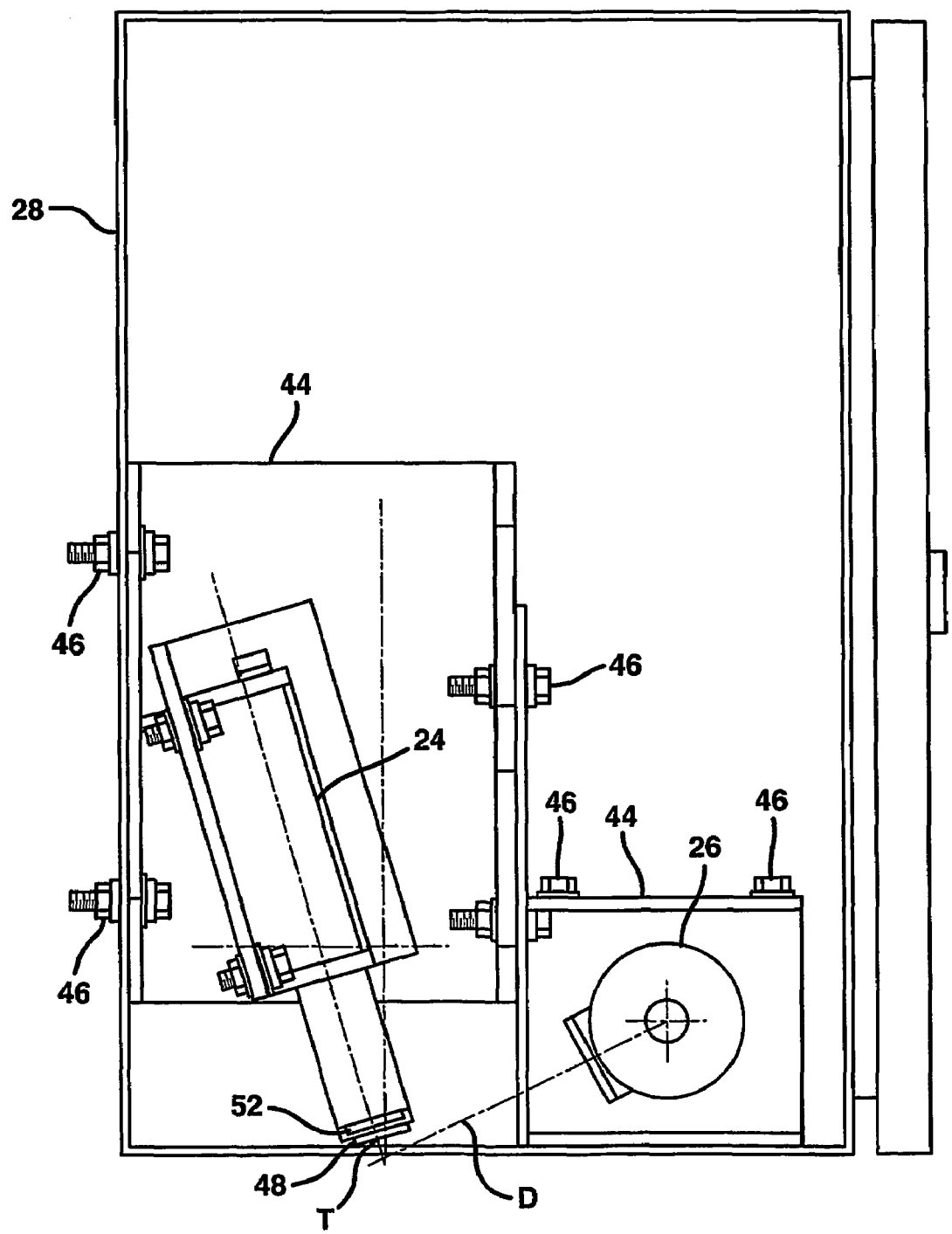
FIG. 3a is a side view showing a preferred source:detector geometry.

FIG. 3a shows a preferred geometry of the X-ray source 24 and detector 26 of the present invention (which are shown in the reversed positions, as compared to FIG. 2). The source 24 is mounted adjacent to the detector 26 such that both are generally directed toward the material for which the analysis is desired, preferably about two inches from the surface thereof (and in some cases, such as when sodium is being measured, less than 0.5 inches). Preferably, the angle between a transmission axis T of the source 24 and a detection axis D of the sensor or detector 26 is an acute angle, preferably between about 65° and 90°, and, most preferably about 78°, while the angle between the transmission axis T and a plane parallel to the sample surface is also an acute angle, most preferably about 57°. To facilitate changing the position (height, spacing, or angle) of either the source 24 and the detector 26, both are independently mounted in an adjustable fashion on stable mounting structures, such as using slotted brackets 44 and corresponding fasteners 46 (e.g., nut and bolt combinations). The particular adjustable mounting used is not considered critical to the invention, as long as the desired geometry is achieved.

Figure 3B:
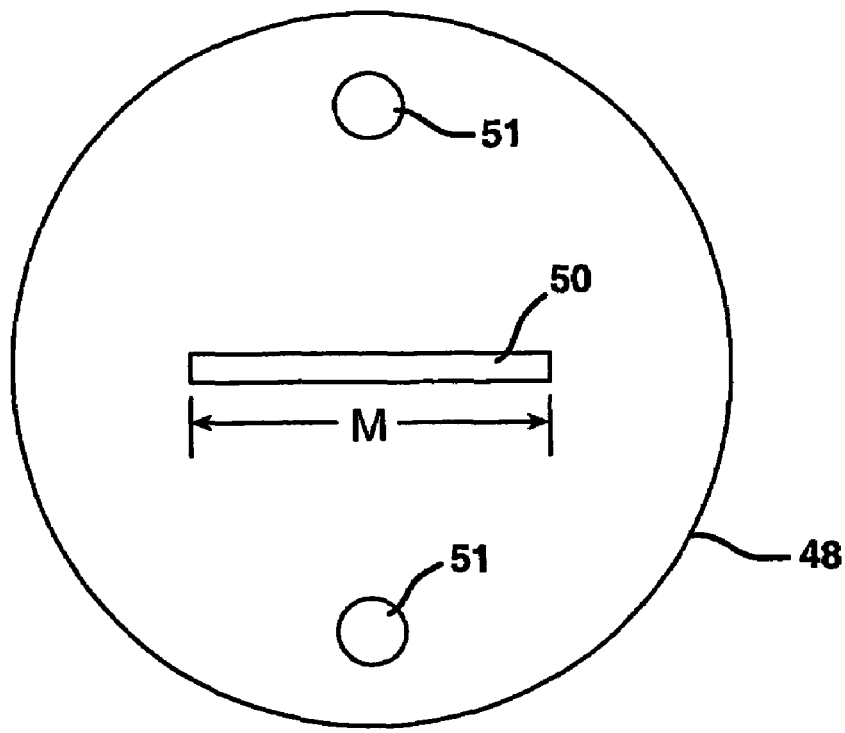
FIG. 3b is an enlarged top plan view showing an example of a collimator for use with the X-ray source of the present invention.

When conveying bulk materials, such as coal, the particles shift laterally across the conveyor 12. Thus, the shape of the interrogation (measuring) zone is more distorted. To reduce the effects of varying profile in the material conveyed past the sensor 10, a collimator 48 may optionally be positioned adjacent to the source 24. Specifically, the collimator 48 is used to collimate the X-rays emitted from the source 24. Preferably, as shown in FIG. 3b, the collimator 48 includes an elongated slot 50 having a major dimension M oriented in the same direction as the material is being conveyed (that is, parallel to the direction in which the material is traveling). The collimator 48 may include openings 51 for facilitating mounting to the X-ray source 24.

Figure 3C:
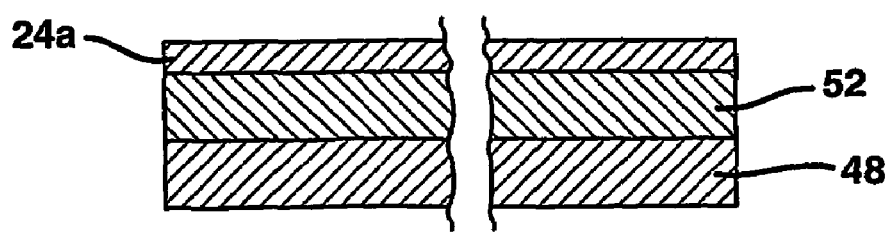
FIG. 3c is a side cross-sectional side view of the positioning of the collimator between the conventional window on the X-ray source and a filter.

To further narrow the bandwidth of incident X-rays in order to excite a particular element(s) with a high degree of efficiency, a filter 52 may also be employed between the X-ray source and the material to be measured. Filter 52 may be comprised of metal and may have a thickness of 10 µm to 4 mm, depending on the energy and intensity of the incident X-rays. As perhaps best shown in FIG. 3c, the filter 52 is preferably interposed between the window 24a on the X-ray source 24 (which is normally made of beryllium) and the collimator 48, if present. Common filter materials are copper, zinc, nickel, zirconium, niobium, molybdenum or any other materials that can eliminate or reduce the X-rays in a particular energy range emanating from an X-ray source. Alloys such as brass can also prove to be effective filters as well. Preferably, the collimator 48 is fabricated of aluminum or the same material as the filter 52.

Figure 4A:
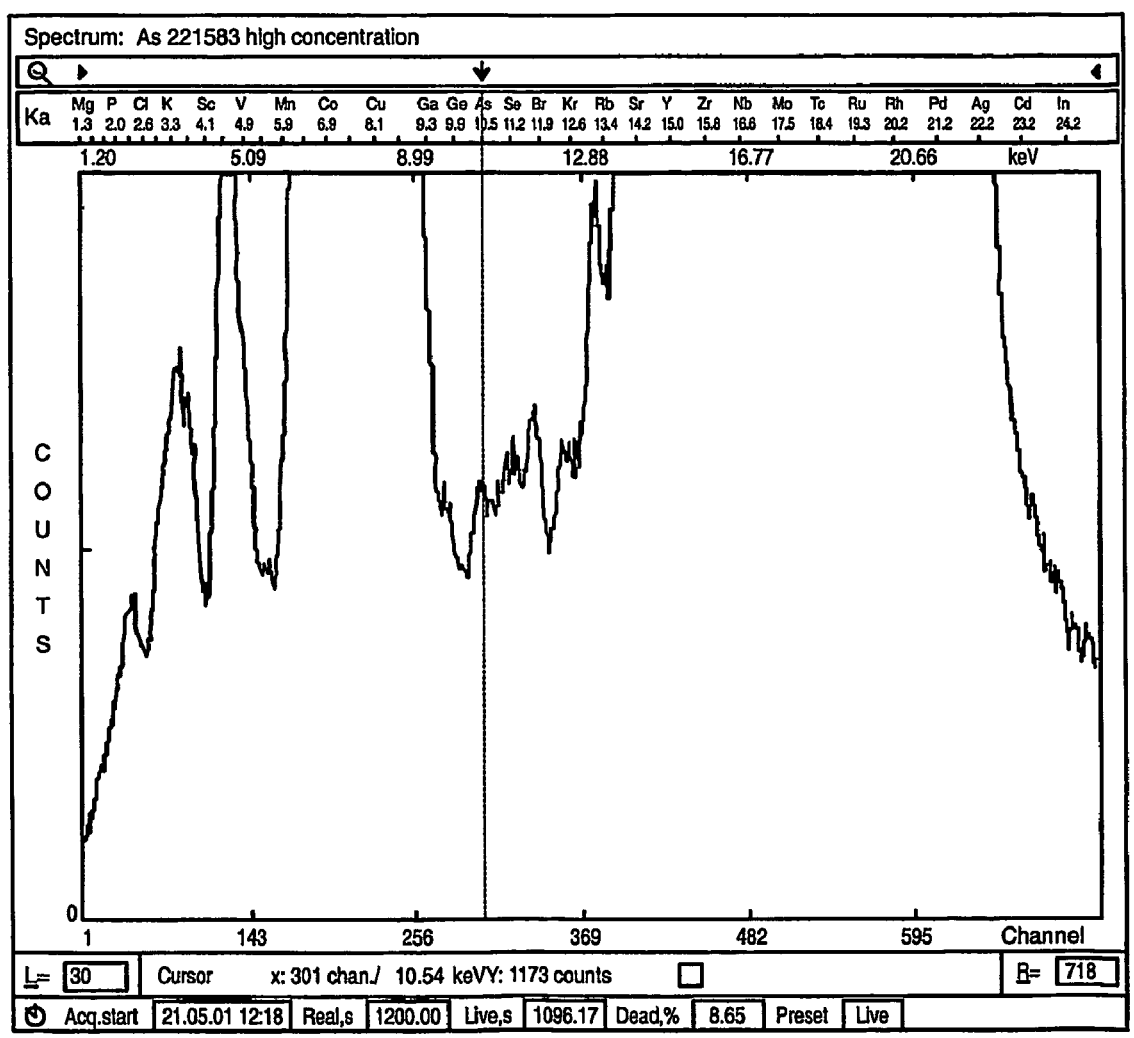
FIG. 4a is a graph showing a broad spectrum generated with the present invention, in which the trace element of interest is arsenic (As)
Figure 4B:
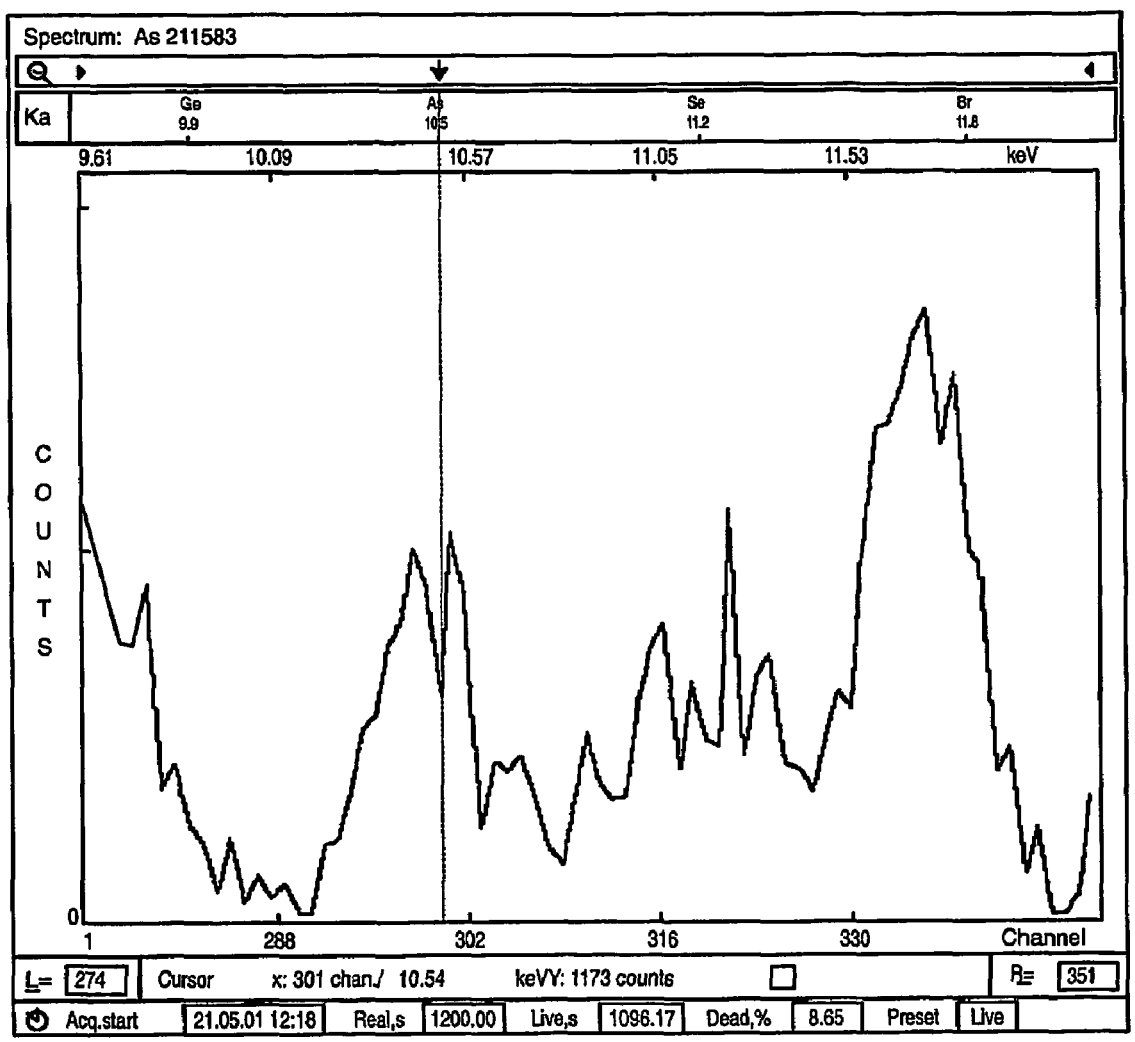
FIG. 4b is an enlargement of the same spectrum showing the resolution of the Kα and Kβ emission bands for arsenic.

Direct measurement of the K and L emission bands from a number of trace elements is possible with the sensor 10 described above. As an example, FIG. 4a shows a broad spectrum generated with the present invention using an X-ray tube as the source 24 with a molybdenum filament, a copper filter 52 mounted next to the tube window 24a, as shown in FIG. 3. The trace element of interest in this case is arsenic (As). FIG. 4b is an enlargement of the same spectrum showing the resolution of the Kα and Kβ emission bands for arsenic. In this sample, the concentration of arsenic was 23 ppm.

Using this sensor 10 with different X-ray energies at less than 80 KeV, preferably less than 65 KeV, still more preferably between 20–65 KeV, and most preferably around 40–45 KeV, it is possible to measure trace elements including vanadium, chromium, manganese, cobalt, nickel, copper, zinc, and molybdenum using the Kα and Kβ emission bands. Mercury and lead Lα emission bands can also be measured using this technique (which could be of great benefit when measuring trace quantities of these metals in water). Other metals, such as platinum and gold dispersed in mineral ores in small or trace quantities can also be measured with low energy (less than 80 KeV) XRF, again using the Lα emission bands.

Figure 5A:
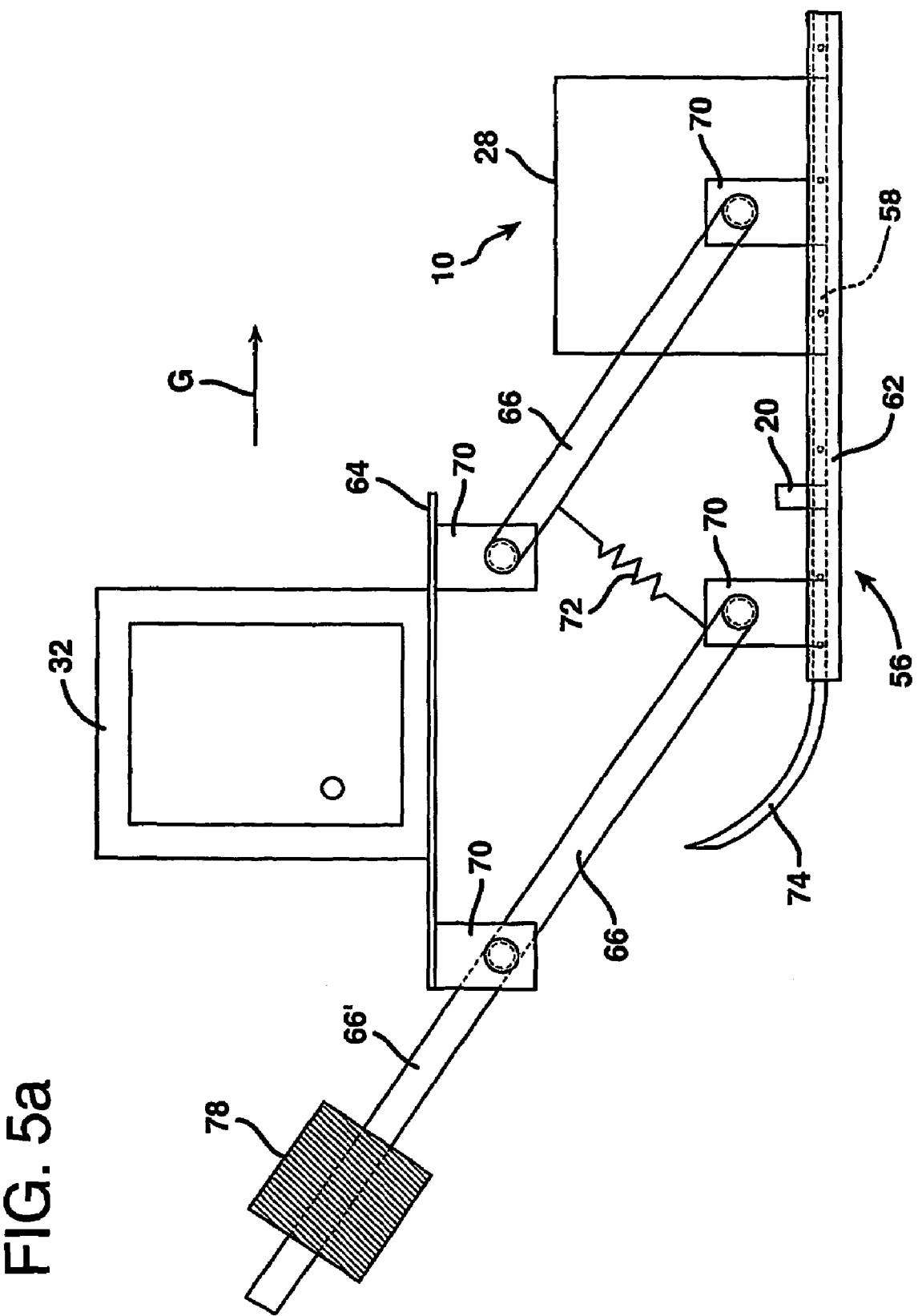
FIG. 5a is shows a side schematic view of a sled for supporting the sensor adjacent to a moving stream of material.

Instead of the arrangements shown in FIGS. 1a and 1b, the XRF trace element sensor 10 described above can be mounted directly adjacent to a moving stream of material on a conveyor (not shown) using a sled 56, as depicted in FIG. 5a. The sled 56 includes a base 58 for assisting in leveling and compacting the material passing underneath the sensor 10 so the profile is substantially constant. The base 58 is sized for supporting the sensor 10 (source/detector) adjacent to an opening 58a (see FIG. 5c), as well as the instrument enclosure 28. The base 58 may also include an opening 58b that may be associated with a sensor 20 for detecting the presence of material adjacent to the sled 56.

Figure 5B:
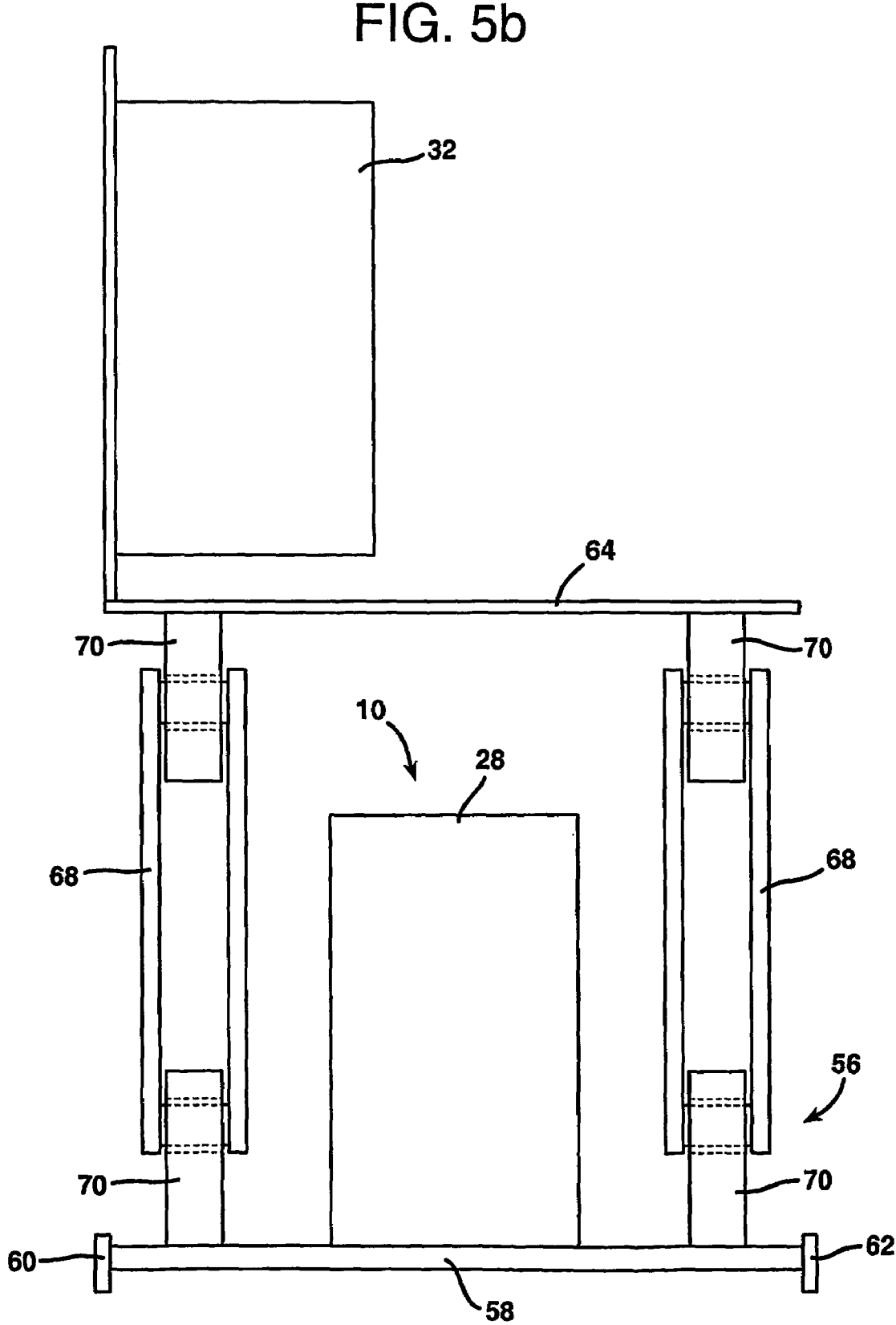
FIG. 5b is a partially cross-sectional end view of another example of a sled for supporting the sensor adjacent to a moving stream of material.
Figure 5C:
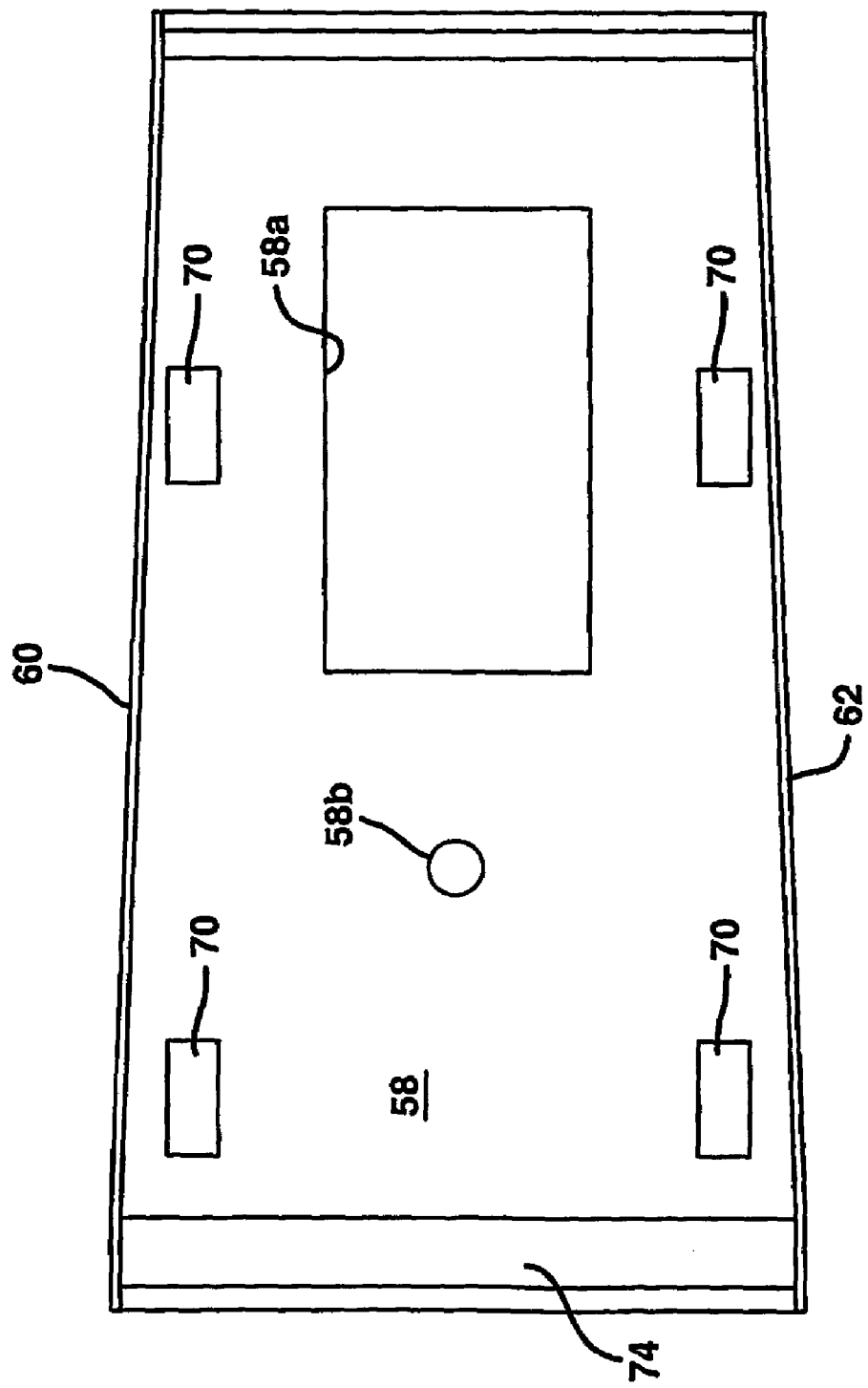
FIG. 5c is a top plan view of one embodiment of the base of the sled.

The sled 56 further includes a pair of elongated runners 60, 62. Each runner 60, 62 may be attached directly to one side of the base 58 (FIG. 5b). As perhaps best shown in FIG. 5c, the runners 60, 62 are preferably converging or narrowing relative to one another along the direction in which the material is traveling (note direction of material travel G in FIG. 5a). As should be appreciated, this further helps to compact the material as it moves towards the sensor 10 positioned downstream from the leading edge of the sled 56. Consequently, the sled 56 is particularly useful with moving streams of material that have a particle size of up to about 50 millimeters, or 2 inches, in size.

The sled 56 is preferably supported by a stable support structure 64 and mounted such that it is capable of moving in response to changes in the geometry or profile of the material being conveyed. In one embodiment, as shown in FIG. 5a, the sled 56 is mounted so as to be capable of swinging to an fro along a generally arcuate path. Specifically, at least two swing arms, and preferably two pairs of swing arms 66 support the sled 56 from the stable support structure 64. The swing arms 66 are mounted to pivot structures 70 at each end such that the sled 56 is capable of swinging to and fro along a generally arcuate path. The mounting is preferably of a type that prevents the ends of the swing arms 66 adjacent to the support structure from moving in the vertical direction (as opposed to the smooth arcuate movement allowed by the pivoting of swing arms 66), which keeps vibrations to a minimum. A shock absorber or damper, such as a spring 72 (represented schematically in FIG. 5a), may also be associated with the sled 56 to resist the swinging movement. For example, the spring 72 may extend between one or both pairs of swing arms 66 on each side of the sled 56, as shown in FIG. 5a. Alternatively, it could be provided between individual swing arms and a stable structure, between the base and a stable structure, or between one or more of the swing arms and the base.

The sled 56 may also include a leveling and smoothing structure 74. Preferably, this structure 74 is mounted along the leading edge of the base 58 and is designed to help compact and smooth the upper surface of the material as it is presented to the onboard sensor 10. It is shown as having a generally arcuate cross-section when viewed from the side, but may have any shape that accomplishes the desired function. A separate smoothing or leveling structure, such as a drum, roller, bar, or the like (not shown) may also be provided upstream of the leading edge of the base 56 of the sled 58. This structure maybe the only leveling structure, or it may be used in combination with structure 74.

As shown in FIG. 5b, the sled 56 may hang freely above the conveyor or other structure along which the material is traveling. Preferably, the sled 56 is positioned such that, in a nominal or free hanging position, it is about 6 inches above the conveyor where the normal bed depth is 8–10 inches. Thus, when the material is on the conveyor at the normal depth, the engagement with the leveling structure 74 causes the sled 56 to move or pivot along an arcuate path, generally in the direction of travel, as shown in FIG. 5a. In this position, it should be appreciated that the weight of the sled 56 still helps to compact the material as it moves toward the sensor 10. This is true even if the spring 72 and counterweight 78 are present.

To facilitate adjusting the position of the sled 56 toward or away from the conveyor, adjustable length arms 66 may be provided. Alternatively, the position of the support structure may be made adjustable, such as by using an adjustable height support frame. In addition, one or both of the leading pair of swing arms 66 may be extended beyond the pivot structure 70 on the distal end (identified with reference numeral 66') and carry or support an adjustable counterweight 78. Consequently, the position of the counterweight 78 along the arm(s) 66' may be adjusted to help counterbalance the weight of the sled 56 (which may be around 200 pounds) to help keep it in intimate contact with the upper surface of the moving stream of material without severely disrupting the flow. This helps to ensure that a more accurate reading is achieved by the sensor 10. The sensor 10 used with the sled 56 need not be for measuring trace elements, but instead could be used for measuring lighter elements, as described in U.S. Pat. No. 6,130,931.

Figure 6:
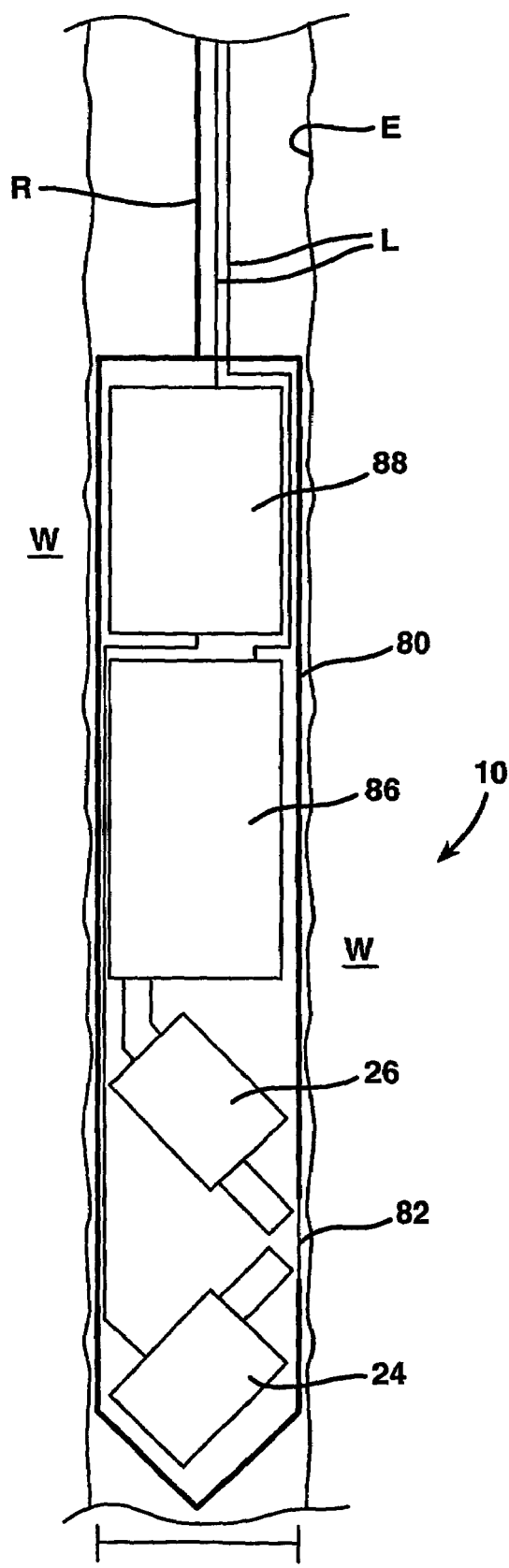
FIG. 6 is a schematic side view showing an embodiment of the sensor for positioning in a borehole.

The sensor 10 may also be used in other possible arrangements, including configurations where the material is stationary. For example, as shown in FIG. 6, the sensor 10 may be in the form of a probe 80 adapted for being positioned or inserted in a borehole E for measuring the elemental composition of the adjacent wall W. Specifically, the X-ray source 24 and X-ray detector 26 are shown as being positioned in a backscatter configuration adjacent to a window 82 formed in the sidewall of the probe 80. The detector 26 may be coupled to an onboard MCA and amplifier 86, while the source 24 is coupled to an onboard power supply 88. The MCA/amplifier 86 and power supply 88 may in turn be coupled to data and power lines L, respectively, emanating from a remote location outside to borehole E. In the case where the borehole E is oriented vertically, a support line, such as a steel rope R, cable, or the like may also be secured to the probe 80 to assist in raising and lowering it. A sensor 10 similar to that shown in FIGS. 1a and 1b could also be mounted on the underside of a chute (not shown) carrying the material past the sensor in a fixed geometry, or it could be mounted to a flow cell to measure concentrations of trace elements in liquids or slurries. The sensor 10 could also be mounted on or adjacent to the cutter head or shearer on a mining machine, such as a highwall miner (not shown) to take measurements from the cutting face. In all cases, the sensor 10 need not be used for measuring trace elements, but instead could be used for measuring lighter elements, as described in U.S. Pat. No. 6,130,931.

Correlation of the element of interest with other elements in the material to correct for matrix effects may be done using a multiple linear regression calibration relationship of the form:

$$E=K_0+K_1C_1+K_2C_2+K_3C_1C_2+K_4C_1^2+K_5C_5+\ldots+K_xC_x+K_yC_y\ldots$$

Where,
E=Element of interest
K=Constant
C=Count rate under a region of interest (peak).

Therefore, combining multiple X-ray sources wherein one is at a first level (e.g., <15 KeV) to cause efficient Kα emission of the "lighter" elements (atomic numbers <30) and a second X-ray source is at a second, higher level (e.g., >15 KeV) to cause efficient Kα emission of the "heavier" elements (atomic numbers >30) provides a system by which matrix effects can be corrected and relationships developed between various elements occurring in a mineral matrix together. This can dramatically improve the accuracy of the measurement. A similar improvement may be gained by using an adjustable voltage X-ray tube, as described above, controlled by a computer or a programmable logic controller (PLC). It is also possible to measure each element in a range of elements, including trace elements, from sodium (atomic number 11) through krypton (atomic number 36) using a properly configured single source.

Figure 7:
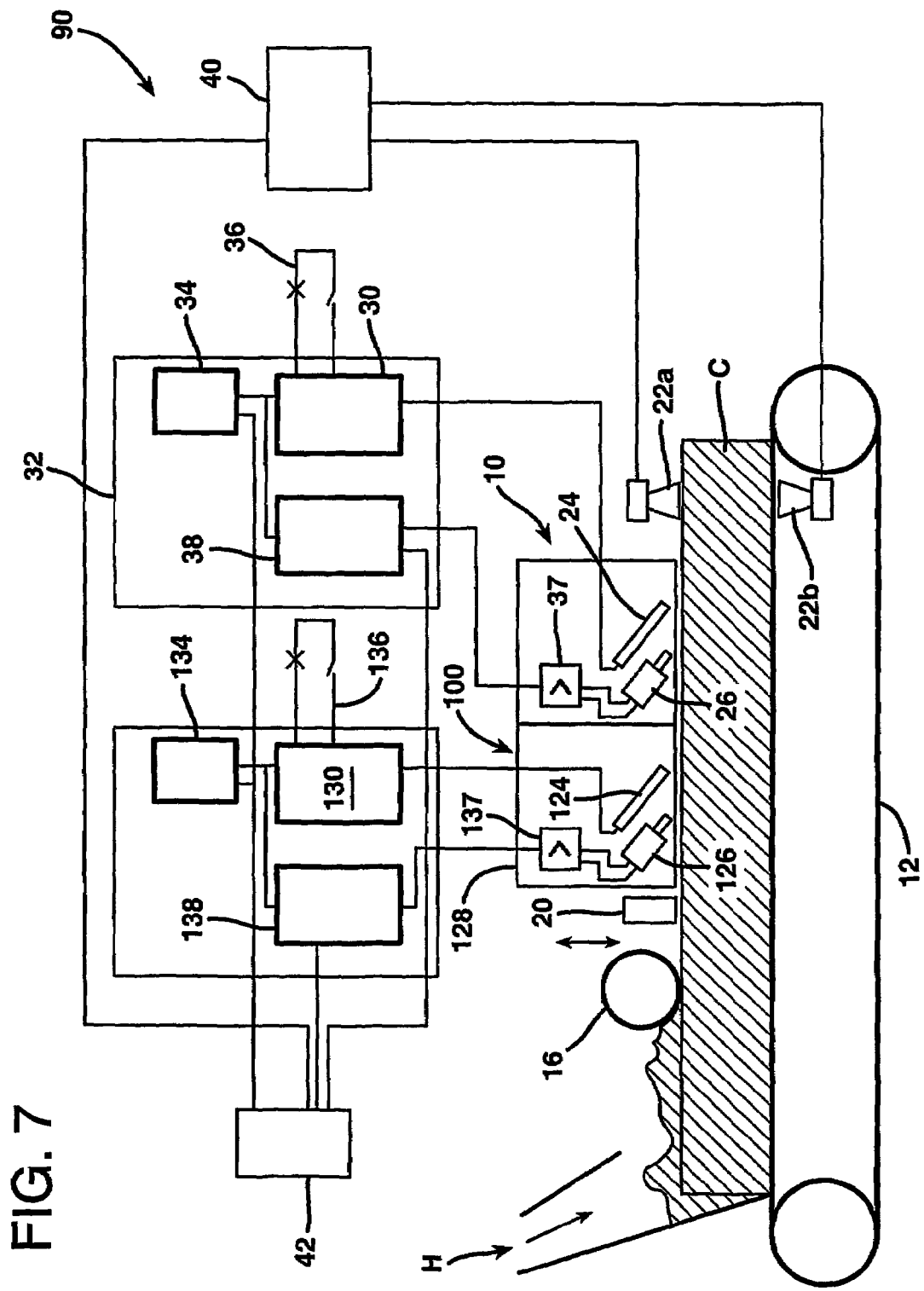
FIG. 7 is a schematic side view of a mechanical sampling system including two sensors positioned inline.

An example of a sampling system 90 including two X-ray sources and detectors for measuring both lighter and heavier elements in the material is shown in FIG. 7 in use adjacent to a moving belt 12. Specifically, the system 90 includes a leveling device, such as drum 16, a first sensor 10 constructed substantially as described in FIG. 1, and moisture sensors 22a, 22b connected to a processor 40. The sensor 10 includes an X-ray source 24 for projecting X-ray energy greater than from about 15 KeV and up to about 65 KeV. Emissions detected by the corresponding detector are processed and sent to a computer 42 to measure the trace elements in the passing stream of material. A substantially identical sensor 100 is positioned in the same or an adjacent instrument enclosure 128, and includes an X-ray source 124 for directing X-ray energy in the range of 3–15 KeV towards the material. The source 124 may be coupled to a high voltage power supply 130 including an interlock 136, and a power supply 134 may also be provided. A second detector 126 detects the fluorescence and sends a second output signal, preferably through a pre-amplifier 137 to an analyzer, such as MCA 138 (which may be powered by a power supply associated with the pre-amplifier). The computer 42 then displays the measured elements corresponding to the range of energies emitted by the second source 124. The second sensor 100 may be substantially identical to the one shown in U.S. Pat. No. 6,130,931.

The foregoing description of several embodiments of the invention have been presented for purposes of illustration and description. The description is not intended to be exhaustive or to limit the invention to the precise form disclosed. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The invention claimed is:

1. A system for the detecting or analyzing of trace elements in a material, comprising:
    at least one X-ray source for directing X-ray energy from greater than 26.4 KeV to less than 59.5 KeV incident on the material;
    at least one detector for detecting X-ray energy fluoresced from the material and producing an output signal in response thereto; and
    an analyzer for indicating the presence of one or more trace elements based on the output signal.

2. The system according to claim 1, wherein the material is coal and the analyzer indicates the presence of one or more trace elements selected from the group consisting of vanadium, chromium, manganese, cobalt, nickel, copper, zinc, arsenic, selenium, molybdenum, mercury, lead, platinum, and gold in the material.

3. The system according to claim 1, further including a filter for filtering the energy emitted from the X-ray source.

4. The system according to claim 3, wherein the filter is formed of a piece of metal having a thickness from between about 10 μm to 4 millimeters and comprised of a material selected from the group consisting of copper, zinc, nickel, zirconium, niobium, molybdenum, and brass.

5. The system according to claim 1, further including a collimator for collimating the X-rays projected from the source to the material.

6. The system according to claim 5, wherein the material is moving in a first direction and the collimator includes an elongated slot having a major dimension that is substantially aligned with the first direction.

7. The system according to claim 1, wherein the X-ray source is an adjustable voltage X-ray tube.

8. The system according to claim 7, further including a computer or programmable logic controller for adjusting the voltage of the X-ray tube.

9. The system according to claim 1, wherein the material is moving, and further including a leveling structure positioned upstream of the X-ray source.

10. The system according to claim 9, wherein the leveling structure is selected from the group consisting of a plow, a rotating drum, a fixed bar, a rotating bar, or combinations thereof.

11. The system according to claim 1, wherein the material is moving and the X-ray source and detector are mounted on a sled in contact with a surface of the material.

12. The system according to claim 1, wherein the X-ray source and detector are positioned in a probe adapted for insertion in a borehole, wherein the material is a portion of a wall defining the borehole.

13. The system according to claim 1, further including a second X-ray source for directing X-ray energy in the range of 3–15 KeV toward the material.

14. A system for the detecting or analyzing of trace elements in a material using an X-ray detector for generating an output signal based on X-ray energy fluoresced by the material, comprising:
- at least one X-ray source for directing X-ray energy from greater than 26.4 Kev to less than 59.5 KeV incident on the material;
- an analyzer for indicating the presence of one or more elements selected from the group consisting of vanadium, chromium, manganese, cobalt, nickel, copper, zinc, arsenic, selenium, molybdenum, mercury, lead, platinum, and gold in the material based on the output signal.

15. The system of claim 14, wherein the detector includes a detection axis and the source includes a transmission axis, wherein the angle between the detection axis and the transmission axis is approximately 78°.

16. A system for the detecting or analyzing of trace elements in a material, comprising:
- at least one X-ray source for directing X-ray energy less than 80 KeV toward the material;
- at least one detector for detecting X-ray energy fluoresced from the material and producing an output signal in response thereto; and
- an analyzer for indicating the presence of one or more elements selected from the group consisting of vanadium, chromium, manganese, cobalt, nickel, copper, zinc, arsenic, selenium, molybdenum, mercury, lead, platinum, and gold in the material based on the output signal;
- wherein the detector includes a detection axis, the source includes a transmission axis, and an angle between the detection axis and the transmission axis is approximately 78°.

17. The system according to claim 16, wherein the detector is mounted within two inches of the material.

18. An apparatus for supporting at least one sensor for intended use in connection with analyzing the elemental composition of a material having a varying profile moving along a conveyor, comprising:
- a base for supporting the sensor adjacent to the conveyor; and
- at least one pair of swing arms supporting the base to allow for movement to and fro along a generally arcuate path as the profile of the material changes.

19. The apparatus according to claim 18, wherein the base includes a pair of spaced, elongated runners for engaging an upper portion of the material moving along the conveyor.

20. The apparatus according to claim 18, wherein the runners are convergent to assist in compacting the portion of the material passing therebetween in a direction generally transverse to the direction in which the conveyor is moving.

21. The apparatus according to claim 18, wherein at least one of the swing arms includes a counterweight for counterbalancing the weight of at least the base such that a selected amount of pressure is applied to the material surface to assist in compaction.

22. The apparatus according to claim 18, wherein the base includes a leveling structure adjacent a leading edge thereof for engaging and smoothing the portion of the material approaching the energy source.

23. The apparatus according to claim 18, wherein at least two pairs of swing arms support the base from a stable support structure positioned above the conveyor.

24. A system for the online detecting or analyzing of trace elements in a material, comprising:
- at least one adjustable voltage X-ray source for directing X-ray energy toward the material;
- at least one detector for detecting X-ray energy fluoresced from the material and producing an output signal in response thereto;
- an analyzer for receiving the output signal; and
- a controller for controlling the voltage of the X-ray source to produce energies at a first predetermined level from 20 KeV to less than 80 KeV and corresponding to the detection of elements in the material having an atomic number less than 30.

25. The system of claim 24, wherein the controller is programmed for controlling the voltage of the X-ray source to produce energies at a second predetermined level corresponding to the detection of elements having an atomic number greater than 30.

26. The system of claim 25, wherein the first energy level is greater than 15 KeV.

27. A system for the online detecting or analyzing of trace elements, comprising:
- a material;
- at least one X-ray source for directing X-ray energy from greater than 26.4 KeV to less than 59.5 KeV incident on the material;
- at least one detector for detecting X-ray energy fluoresced from the material and producing an output signal in response thereto; and
- an analyzer for receiving the output signal and indicating the presence of one or more elements selected from the group consisting of vanadium, chromium, manganese, cobalt, nickel, copper, zinc, arsenic, selenium, molybdenum, mercury, lead, platinum, and gold in the material.

28. The system of claim 27, wherein the material is comprised of particles having an average size of greater than 10 millimeters.

29. The system of claim 27, wherein the material is water.

30. A method for analyzing the elemental composition of a material, comprising:
- using an X-ray source to strike the material with X-ray energy from greater than 26.4 KeV to less than 59.5 KeV;
- detecting X-ray fluorescence from the material; and
- analyzing the fluorescence to determine the presence of one or more trace elements.

31. The method according to claim 30, wherein the analyzing step includes detecting the presence of elements selected from the group consisting of vanadium, chromium, manganese, cobalt, nickel, copper, zinc, arsenic, selenium, molybdenum, mercury, lead, platinum, and gold in the material.

32. The method of claim 30, wherein the presence of vanadium, chromium, manganese, cobalt, nickel, copper, zinc, arsenic, selenium, molybdenum is detected by measuring the Kα or Kβ emission bands.

33. The method of claim 30, wherein the presence of mercury, lead, platinum, and gold is detected by measuring the Lα emission bands.

34. The method of claim 30, wherein the method further includes mounting an X-ray source and detector in a probe for positioning in a borehole.

35. The method of claim 30, wherein the method further includes mounting an X-ray source and detector on a mining machine.

36. A method of completing online elemental analysis on a material, comprising:
using an adjustable voltage X-ray tube to project X-ray energy toward the material at a first level selected from the range of 20 KeV to 80 KeV for detecting the presence of one or more trace elements;
detecting the X-ray energy fluoresced by the material; and
adjusting the voltage of the X-ray tube to project X-ray energy toward the material at a second level different from the first level.

37. The method of claim 36, further including the step of detecting the X-ray energy fluoresced from the material after the adjusting step.

38. A method of positioning a sensor for use in connection with elemental analysis closely adjacent to a material moving along a conveyor, comprising:
positioning a structure capable of swinging to and fro adjacent to an upper surface of the material moving along the conveyor; and
mounting the sensor on the structure.

39. The method of claim 38, wherein the structure is a sled including a pair of convergent runners, the sensor comprises an X-ray source and an X-ray detector, and the mounting step includes mounting the X-ray source and detector in a backscattering geometry between the runners.

40. A system for the detecting or analyzing of trace elements in a material, comprising:
at least one adjustable voltage X-ray tube for directing X-ray energy from between 20 KeV to less than 80 KeV toward the material;
at least one detector for detecting X-ray energy fluoresced from the material and producing an output signal in response thereto; and
an analyzer for indicating the presence of one or more elements based on the output signal.

41. The system of claim 40, further including a sled for supporting the adjustable voltage X-ray tube.

42. A system for the detecting or analyzing of trace elements in a material, comprising:
at least one X-ray source for directing X-ray energy toward the material;
at least one detector for detecting X-ray energy fluoresced from the material and producing an output signal in response thereto; and
wherein the X-ray source and detector are mounted on a sled in contact with a surface of the material.

43. The system of claim 42, wherein the sled is supported by a plurality of swing arms.

44. A method for assessing the presence of mercury or arsenic in coal, comprising:
striking the coal with X-ray energy from greater than 20 KeV to 80 KeV;
detecting X-ray fluorescence from the coal; and
analyzing the fluorescence to determine the presence of mercury or arsenic in the coal.

45. The method of claim 44, wherein the X-ray energy level incident on the material is about 25 KeV.

\* \* \* \* \*

UNITED STATES PATENT AND TRADEMARK OFFICE
CERTIFICATE OF CORRECTION

PATENT NO.         : 7,200,200 B2                                     Page 1 of 1
APPLICATION NO. : 10/488723
DATED              : April 3, 2007
INVENTOR(S)        : Melvin J. Laurilla and Claus C. Bachmann It is certified that error appears in the above-identified patent and that said Letters Patent is hereby corrected as shown below:

Claim 22, col. 10, line 8, before the term "material", insert -- approaching --.

Claim 22, col. 10, line 9, delete "approaching the energy source".

Claim 28, col. 10, line 49, please replace "greater than" with -- less than or equal to --.

Signed and Sealed this

Fifth Day of June, 2007

JON W. DUDAS
*Director of the United States Patent and Trademark Office*

(12) EX PARTE REEXAMINATION CERTIFICATE (8755th)
United States Patent
Laurila et al.

(10) Number: US 7,200,200 C1
(45) Certificate Issued: Dec. 13, 2011

(54) X-RAY FLUORESCENCE MEASURING SYSTEM AND METHODS FOR TRACE ELEMENTS

(75) Inventors: Melvin J. Laurila, Georgetown, KY (US); Claus C. Bachmann, Bad Wilbad (DE)

(73) Assignee: Quality Control, Inc., Lexington, KY (US)

Reexamination Request:
No. 90/009,460, Jun. 18, 2009

Reexamination Certificate for:
Patent No.: 7,200,200
Issued: Apr. 3, 2007
Appl. No.: 10/488,723
Filed: Mar. 3, 2004

Certificate of Correction issued Jun. 5, 2007.

(22) PCT Filed: Sep. 3, 2002

(86) PCT No.: PCT/US02/27815
§ 371 (c)(1),
(2), (4) Date: Mar. 3, 2004

(87) PCT Pub. No.: WO03/021244
PCT Pub. Date: Mar. 13, 2003

Related U.S. Application Data

(60) Provisional application No. 60/317,257, filed on Sep. 4, 2001.

(51) Int. Cl.
*G21N 23/223* (2006.01)

(52) U.S. Cl. .................... 378/45; 250/269.3; 378/47
(58) Field of Classification Search .............. 378/45
See application file for complete search history.

(56) References Cited

To view the complete listing of prior art documents cited during the proceeding for Reexamination Control Number 90/009,460, please refer to the USPTO's public Patent Application Information Retrieval (PAIR) system under the Display References tab.

*Primary Examiner* — Minh T Nguyen

(57) ABSTRACT

An X-ray fluorescence measuring system and related measuring methods are disclosed, the system using X-ray energy at a level of less than 80 KeV may be directed toward a material, such as coal. The energy fluoresced may be detected (10) and used to measure the elemental composition of the material, including trace elements. The material may be moving or stationary.

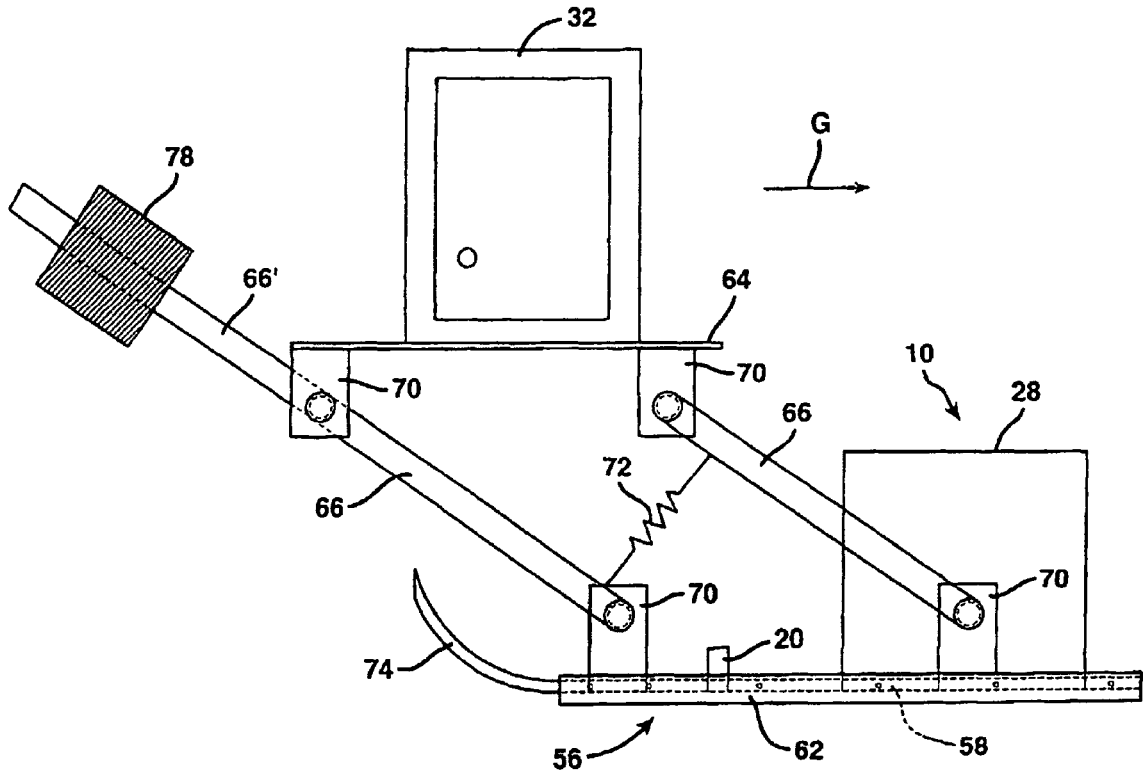

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 10-12, 15-16, 18-23, 27-29 and 36-45 are cancelled.

Claims 1-2, 9, 14, 17, 24, 26 and 30-34 are determined to be patentable as amended.

Claims 3-8, 13, 25, and 35, dependent on an amended claim, are determined to be patentable.

New claims 46-61 are added and determined to be patentable.

1. A system for the detecting or analyzing of trace elements [in a material], comprising:
   *a material*, at least one X-ray source for directing X-ray energy from greater than 26.[4] *7* KeV to less than [59.5] *30* KeV incident on the material;
   at least one detector for detecting X-ray energy fluoresced from the material and producing an output signal in response thereto; and
   an analyzer for indicating the presence of one or more trace elements based on the output signal;
   *wherein the material is moving and the X-ray source and detector are mounted on a sled in contact with a surface of the material.*

2. The system according to claim 1, wherein the material is coal *comprised of particles having a size of less than or equal to 10 millimeters* and the analyzer indicates the presence of one or more trace elements selected from the group consisting of [vanadium, chromium, manganese, cobalt, nickel, copper, zinc,] arsenic, [selenium, molybdenum,] mercury, [lead,] platinum, and gold in the material.

9. The system according to claim 1, [wherein the material is moving, and] further including a leveling structure positioned upstream of the X-ray source.

14. A system for the detecting or analyzing of trace elements in a material using an X-ray detector for generating an output signal based on X-ray energy fluoresced by the material, comprising:
   at least one X-ray source for directing X-ray energy from greater than 26.[4] *7* Kev to less than [59.5] *30* KeV incident on the material;
   an analyzer for indicating the prresence of one or more elements selected from the group consisting of [vanadium, chromium, manganese, cobalt, nickel, copper, zinc,] arsenic, [selenium, molybdenum,] mercury, [lead,] platinum, and gold in the material based on the output signal;
   *wherein a filament of the X-ray source is selected to keep characteristic X-ray emissions from the filament material from masking a peak from a trace element.*

17. The system according to claim [16]*1*, wherein the detector is mounted within two inches of the material.

24. A system for the online detecting or analyzing of trace elements in a material, comprising:
   at least one adjustable voltage X-ray source for directing X-ray energy toward the material *at an energy level within the range of 1.5-3.0 times the energy of the characteristic emission bands from the element of interest*;
   at least one detector for detecting X-ray energy fluoresced from the material and producing an ouput signal in response thereto;
   an analyzer for receiving the output signal; and
   a controller for controlling the voltage of the X-ray source to produce energies at a first predetermined level from 20 KeV to less than 80 KeV and corresponding to the detection of elements in the material having an atomic number less than 30.

26. The system of claim 25, wherein the [first] *second* energy level is greater than 15 KeV.

30. A method for analyzing the elemental composition of [a material] *coal*, comprising:
   using an X-ray source to strike the [material] *coal* with X-ray energy from greater than 26.4 KeV to less than 59.5 KeV, *wherein the X-ray source is adjusted to produce energy within the range of 1.5-3.0 times the energy of characteristic emission bands from at least one element of interest*;
   detecting X-ray fluorescence from the material; and
   analyzing the fluorescence to determine the presence of one or more trace elements.

31. The method according to claim 30, wherein the analyzing step includes detecting the presence of elements selected from the group consisting of [vanadium, chromium, manganese, cobalt, nickel, copper, zinc,] arsenic, [selenium, molybdenum,] mercury, [lead,] platinum, and gold in the material.

32. The method of claim 30, wherein the presence of [vanadium, chromium, manganese, cobalt, nickel, copper, zinc,] arsenic[, selenium, molybdenum] is detected by measuring the Kα or Kβ emission bands.

33. The method of claim 30, wherein the presence of mercury, [lead,] platinum, and gold is detected by measuring the Lα emission bands.

34. The method of claim 30, wherein the method further includes [mounting an X-ray source and detector in a probe for positioning in a borehole] *filtering the X-ray energy to narrow the band of incident X-rays*.

46. *The system according to claim 24, further including a second X-ray source for directing X-ray energy toward the material.*

47. *The system according to claim 46, wherein the controller controls the second X-ray source to produce energies at a second predetermined level less than 20 keV.*

48. *A method for analyzing elemental composition of coal, comprising:*
   *using an X-ray source to strike coal with X-ray energy from greater than 26.4 KeV to less than 45 KeV, wherein the energy from the X-ray source is adjusted to produce energy within the range of 1.5-3.0 times the energy of the characteristic emission bands from an element of interest;*
   *detecting X-ray fluorescence from the coal; and*
   *analyzing the fluorescence to determine the presence of an element selected from the group consisting of arsenic, mercury, gold, and platinum.*

49. The method of claim 48, wherein the detecting step comprises detecting X-ray fluorescence with an X-ray fluorescence detector positioned about two inches from the coal.

50. The method of claim 48, wherein the X-ray source is a first X-ray source, and further including the step of using a second X-ray source to strike the coal with X-ray energy.

51. The method of claim 50, wherein the step of using the second X-ray source comprises striking the coal with X-ray energy from the second source in the range of 3-20 keV.

52. The method of claim 50, further including the step of analyzing the fluorescence resulting from the striking of the coal with energy from the second X-ray source to determine the presence of an element having an atomic number less than 30.

53. The method of claim 48, further including the step of filtering the X-ray energy to narrow the band of incident X-rays.

54. A system for the detecting or analyzing of trace elements in a material, comprising:

at least one adjustable voltage X-ray tube for directing X-ray energy from between 20 KeV to less than 80 KeV toward the material;

at least one detector for detecting X-ray energy fluoresced from the material and producing an output signal in response thereto; and an analyzer for indicating the presence of one or more trace elements based on the output signal, wherein a filament of the X-ray tube is selected to keep characteristic X-ray emissions from the filament material from masking a peak from a trace element.

55. The system of claim 54, wherein the filament comprises molybdenum.

56. The system of claim 54, further including a filter for filtering the X-ray energy from the source.

57. A system for the detecting or analyzing of trace elements, comprising:

a material; at least one X-ray source for directing X-ray energy from greater than 20 KeV to less than 80 KeV incident on the material and within the range of 1.5-3.0 times the energy of the characteristic emission bands from the element of interest;

at least one detector for detecting X-ray energy fluoresced from the material and producing an output signal in response thereto; and an analyzer for indicating the presence of one or more trace elements based on the output signal.

58. The system of claim 57, wherein the material is water.

59. The system of claim 57, wherein the energy directed from the X-ray source is in a range from greater than 20 KeV to less than 35 KeV.

60. The system of claim 57, wherein the element of interest includes one of arsenic, mercury, gold, and platinum.

61. A method of analyzing an elemental composition of a material, comprising:

striking the material with X-ray energy from an X-ray source in a range from greater than 20 KeV to less than 80 KeV; detecting X-ray fluorescence from the material; and analyzing the fluorescence to determine the presence of an element selected from the group consisting of arsenic, mercury, gold, and platinum; wherein the X-ray source is adjusted to produce energy within the range of 1.5-3.0 times the energy of the characteristic emission bands from the selected element.

* * * * *